United States Patent [19]

Bessler

[11] Patent Number: 4,588,745

[45] Date of Patent: May 13, 1986

[54] TREATMENT OF VEGETABLE OILS

[75] Inventor: Terry R. Bessler, Decatur, Ill.

[73] Assignee: A. E. Staley Manufacturing Company, Decatur, Ill.

[21] Appl. No.: 601,189

[22] Filed: Apr. 17, 1984

[51] Int. Cl.$^4$ ............................................. A61K 31/23
[52] U.S. Cl. ................................................... 514/552
[58] Field of Search ................ 424/312, 199; 514/552, 514/78

[56] References Cited

U.S. PATENT DOCUMENTS

| | | | |
|---|---|---|---|
| 2,819,199 | 1/1958 | Kalish | 424/312 |
| 2,945,869 | 7/1960 | Meger et al. | 424/312 |
| 2,977,283 | 3/1961 | Meger et al. | 424/312 |
| 3,798,246 | 3/1974 | Shimazaki et al. | 260/403 |
| 4,101,673 | 7/1978 | Chang | 424/312 |
| 4,280,999 | 7/1981 | Okamoto et al. | 424/199 |
| 4,425,276 | 1/1984 | Gauther | 260/403 |

OTHER PUBLICATIONS

Jensen et al., Lipids 1, No. 6 (1966), pp. 451–452.
Singleton et al, J. Am. Oil Chem. Soc. (1966) 43(10), pp. 592–595.
Min et al, J. Am. Oil Chem Soc. (1972) 49(12), pp. 675–677.

*Primary Examiner*—Stanley J. Friedman
*Assistant Examiner*—John W. Rollins, Jr.
*Attorney, Agent, or Firm*—Michael F. Campbell; James B. Guffey; Philip L. Bateman

[57] ABSTRACT

A process for preparing triglycerides which are suitable as a lipid base for an injectable composition is described.

7 Claims, No Drawings

TREATMENT OF VEGETABLE OILS

BACKGROUND OF THE INVENTION

1. Field of the Invention

This invention relates to oil-based compositions which are suitable for injection.

2. Description of the Art Practices

U.S. Pat. No. 4,280,996 issued July 28, 1981 to Okamoto et al, describes a stable fat emulsion which is suitable as a nutritive infusion fluid. The composition in the Okamoto et al patent is stated to be useful in that it is rapidly metabolized from the blood. The patent of Meyer et al, U.S. Pat. No. 2,977,283 issued Mar. 28, 1961, describes therapeutic fat products which are stated to be suitable for intravenous use in human beings.

Phosphatide emulsifying agents are described by Meyer et al in U.S. Pat. No. 2,945,869 issued July 19, 1960. Further disclosures of oil-containing products are found in U.S. Pat. No. 2,819,199 issued Jan. 7, 1958 to Kalish.

The purification of oils for the removal of undesirable colors and odors is described in U.S. Pat. No. 3,798,246 issued Mar. 19, 1974 to Shimazaki et al. In the U.S. Pat. No. 3,798,246, the use of silica gel in combination with an eluting organic solvent is described. Gunther, in U.S. Pat. No. 4,425,276 issued Jan. 10, 1984 describes a separation of the various components of an oil through the use of silicic acid gels in combination with lower alkanols. Gunther suggests that the purified oils will be useful for pharmaceutical purposes. The oils of Gunther are processed at temperatures up to 70° C. in the presence of the alkanol.

Chang, in U.S. Pat. No. 4,101,673 issued July 18, 1978, states that the parental administrable oil-in-water emulsions from soybean oil may be obtained by first treating the oil with silicic acid or silica gel. Chang further describes including gamma tocopherol and ascorbyl palmitate to function respectively as an antioxidant and as a metal scavenging agent in his oil. The purification of triglycerides is suggested in an article entitled "Purification of Triglycerides With an Alumina Column" by Jensen et al which has been reported in *Lipids*, Vol. 1, No. 6, (1966) page 451 et seq. An article entitled "Isolation and Identification of trans-3,5-Dimethoxystilbene from High Quality Tall Oil Fatty Acids by Liquid Chromatography and Mass Spectrometry" describes the use of liquid column chromatography for low temperature solvent fractionation of an oil. The above article is published in *J. Am. Oil Chem. Soc.* (1972) Vol. 49 (12), pp. 675–677 by Min et al.

The treatment of cottonseed oil is reported in an article entitled "A Method for Adsorbent Fractionation of Cottonseed Oil for Experimental Intravenous Fat Emulsions" by Singleton et al, which is reported in *J. Am. Oil Chem. Soc.* (1966), Vol. 43 (10), pp. 592–595. The Singleton et al article describes the use of a mixture of bleaching earth and alumina as a fractionation method for removal of pigments and polar components of cottonseed oil.

The foregoing references to the extent applicable to the present invention are herein incorporated by reference. Percentages and ratios given herein are by weight, temperatures are in degrees Celsius and pressures are in atmospheres above ambient unless otherwise indicated.

SUMMARY OF THE INVENTION

A process is described for preparing an injectable vegetable oil selected from the group consisting of soybean oil and sunflower oil and mixtures thereof which comprises:

(a) first treating the oil with an acid clay;
(b) deodorizing the vegetable oil;
(c) treating the deodorized oil with an acid clay to reduce the content of a member selected from the group consisting of diglycerides, tocopherol components, and trilinolenin and mixtures thereof; and
(d) thereafter conducting a particulate filtration to remove a substantial portion of the acid clay, thereby obtaining the injectable vegetable oil.

An injectable oil product is described which is a triglyceride with each fatty acid in the ester having from 12 to 20 carbon atoms; having higher free fatty acid content; having reduced trilinolenin content; having reduced diglyceride content and reduced natural tocopherol content based on the starting oil.

DETAILED DESCRIPTION OF THE INVENTION

The present invention first requires an oil (triglyceride) which is suitable for injection. The present invention preferentially uses soy or sunflower oils as the raw material. Each of the oils are commercially available. A material such as cottonseed oil is undesirable due to its high gossypol content. The gossypol in cottonseed oil is toxic and therefore its inclusion requires a greater degree of processing to remove the toxicity from the oil to render the oil suitable for injection. As the oil is to be used for injectable purposes, the beneficiaries of this invention are persons who are ordinarily in a weakened state and anything other than a substantially pure oil is of critical importance.

The oils as referred to above are triglyceride materials. The fatty acid portion of the esters is substantially the same as that found in commercial soy or sunflower seed oil, i.e. $C_{12}$ to $C_{20}$. In the present invention, the trilinolenin content is reduced in the processing and therefore this component is present in lower quantities than is ordinarily found in the starting oils. Trilinolenin is the trilinolenic acid ester of glycerin.

Typically, the oil for use in the present invention has been obtained by crushing the oilseed followed by hexane extraction of the oil to give the crude oil. The crude oil is then hydrated with a small amount of water to remove the gum-forming components. Gum-forming components are synonymous with lecithin or phosphatides. The degummed oil is then caustic-refined to reduce the phosphatides further. Free fatty acids are also removed by the caustic-refining through saponification to a soap.

In continuing with commercial processing, the once-refined oil, that being defined as the oil following caustic treatment, is bleached and then deodorized.

In the present invention, the processing is substantially similar up to the point where the once-refined oil is obtained. Thereafter, the once-refined oil is treated with an acid clay.

Suitable acid clays for use in the present invention include materials such as TONSIL OPTIMUM FF, TONSIL OPTIMUM EXTRA FF or TONSIL L-80. In particular, montmorillonite clays should be utilized and such materials typically have a constitution of from 60 to 85% by weight $SiO_2$; 10 to 20% aluminum oxide;

1 to 8% ferric oxide; 0.5 to 2.5% magnsium oxide; 0.4 to 1.5% calcium oxide and 7.2% volatiles by ignition loss. Other suitable acid clays include any which exhibit typical acid behavior as does the aforedefined clay. It is necessary herein that an acid clay be utilized as it is desirable to increase the measured free fatty acid content of the end product beyond that which would be found in an ordinarily processed oil.

The oil is acid clay treated as defined in step (a) of the present invention, preferably at a temperature of from about 80° C. to about 130° C., most preferably from about 95° C. to about 115° C. The acid clay is added to the vegetable oil in the absence of any solvents and therefore, extraneous solvents are avoided. It is noted, however, that the oils of the present invention have been obtained by hexane extraction in the first instance, however, the hexane has been removed due to routine processing and any residual components are further removed by the processing of the present invention.

The next step (b) of the present invention is to deodorize the vegetable oil. Deodorizing is commonly conducted on vegetable oils to make them palatable to the human taste. In the present case, the deodorizing is conducted to remove various unwanted pigments and other components. As the oils must be injectable, the deodorizing step herein is not conducted to make the oil palatable but rather to remove components which may otherwise interfere with the treatment prescribed by the injectable oil. The deodorization does remove a substantial amount of the free fatty acids, aldehydes, pigments and pest-control agents present in the oil.

The deodorizing step in the present invention consists of treating the oil with steam and applying a vacuum to remove volatilized components. The deodorization step is conducted at from about 220° C. to about 280° C., preferably from about 240° C. to about 260° C.

After the vegetable oil has been steam-deodorized, a second treatment with an acid clay is conducted. The acid clay at this portion of the invention is conveniently added in a weight ratio to the oil of from about 1:99 to about 1:1, most preferably from about 1:19 to about 1:4. The purpose of the second acid clay treatment is to remove a member selected from the group consisting of diglycerides, tocopherol, and trilinolenin.

The foregoing components are believed to be detrimental to the effectiveness of the oil as an injectable medium. It is also noted at this point that the free fatty acid content of the vegetable oils is slightly increased upon the second acid clay treatment. It is believed that the increase in free fatty acid content is partially due to acid hydrolysis of the triglyceride oil. Thus, the injectable oil of the present invention will have a higher free fatty acid content than is found in ordinary oils. The free fatty acid content of the injectable oil is from about 0.005% to about 0.015% by weight of the oil.

The second treatment (c) with an acid clay is conducted at from about 10° C. to about 60° C., preferably from about 25° C. to about 45° C. The second acid clay treatment of the oil is advantageously conducted at the lower temperature thereby ensuring that unwanted by-products do not form. One positive material which is formed during the acid clay treatment is the free fatty acids which are generated in amounts higher than that found in an ordinary vegetable oil. The process herein advantageously has a slightly higher than ordinary amount of fatty acids therein because the free fatty acids are already partially digested. Therefore, nutritional needs are fulfilled more easily by the body not having to hydrolyze triglyceride into the essential fatty acids. Trilinolenin breakdown would not produce any essential fatty acids. Diglycerides are known emulsifiers and may alter both the emulsion that is injected and affect absorption from the bloodstream into tissues.

The final step in processing the injectable oil of the present invention is to conduct a filtration of the oil sufficient to remove substantially all of the acid clay utilized in the process. This, of course, ensures that no particles which could interfere with the desirable properties of the injectable oil will be present in the finished product. Preferably, the filtration is conducted through a pore size filter of from about 0.1 to 0.45 microns, preferably from about 0.15 to about 0.25 microns. Suitable filtering materials include sterilized membrane cartridges supplied by Gelman Sciences Filtration Equipment, Inc. The filters are of a size that they function as microbial filters.

A suggested embodiment of the present invention is hereafter disclosed. The injectable oil obtained from the example may be utilized in any conventional manner for forming an oil-based injectable composition.

EXAMPLE I

A degummed and caustic refined triglyceride oil obtained from crushed soybeans is slurried with 0.5% acid clay by weight of the oil at 115° C. with agitation for about 30 minutes. The oil is then steam-deodorized. A column is prepared which is packed with 10 parts of montmorillonite clay having substantially the same composition as previously indicated in the specification. The oil at 90 parts is passed through the column using nitrogen at slightly greater than atmospheric pressure to elute the oil. The recovered oil is then passed through a 0.45 micron membrane filter to remove the acid clay and any microorganisms.

The oil has increased free fatty acid content and decreased tocopherol, diglyceride and trilinolenin contents. The recovered oil is suitable for use in an injectable composition.

If desired, the tocopherol which is removed in the present invention may be added back as either a source of natural or synthetic vitamin E.

EXAMPLE II

A mixture of a triglyceride vegetable oil wherein the average carbon chain length of the fatty acid components of the triglyceride is from about 14 to about 18 carbon atoms is mixed with 0.3% of Filtrol 105 acid clay by weight of the oil. The mixture is agitated at 115° C. for one-half hour. The product is thereafter pumped through a plate and frame filter press at about 1.5 atmospheres over ambient.

The oil is then sent to a steam distillation apparatus and steam-sparged to reduce the free fatty acid content.

The oil at 90 parts is then mixed with Tonsil Optimum FF acid clay at 10 parts and processed at 20° C. to 45° C. The oil is further recovered as previously described to give a suitable injectable oil.

The foregoing example may be modified by passing the product through a column in the second step instead of mixing the oil with the acid clay. In either case, it is advantageous to process the oil through the acid clay at a temperature of from about 20° C. to 45° C. which is below the temperature first utilized for the acid clay treatment.

The clays which are suitable herein are available from L. A. Salomon & Bro., Port Washington, N.Y.

The clays have the following physical parameters in Table I.

TABLE 1

| | OPTIMUM EXTRA | OPTIMUM | L-80 |
|---|---|---|---|
| Bulk Density (max.) | 0.02 lb/cu. in. | 0.020 | 0.023 |
| Free Moisture (max.) | 12% | 10% | 10% |
| Acidity (max.) | 0.4% | 0.04% | 0.02% |
| Filtration Speed (max.) | 2'/100 cm$^3$ | 2'/100 cm$^3$ | 2'/100 cm$^3$ |
| Oil Retention (max.) | 40% | 40% | 36% |
| pH (max.) | 3.5 | 4.5 | 7.0 |
| Surface area (min.) | 200 m$^2$/g | 180 m$^2$/g | 160 m$^2$/g |
| Particle Sizes | | | |
| Stays on mesh 100 (max.) | 4% | 4% | 3% |
| Stays on mesh 200 (max.) | 20% | 20% | 20% |
| Stays on mesh 230 (max.) | 25% | 25% | 25% |
| Stays on mesh 325 (max.) | 40% | 40% | 35% |
| Stays on 25 microns (max.) | 75% | 75% | 75% |
| Chemical Analysis | | | |
| SiO$_2$ % (min.-max.) | 68–73 | 69–74 | 68–73 |
| Al$_2$O$_3$ % (min.-max.) | 9–12 | 10–13 | 11–14 |
| Fe$_2$O$_3$ % (min.-max.) | 1–3 | 3–5 | 3–5 |
| Na$_2$O % (min.-max.) | 0–1 | 0–2 | 0–2 |
| MgO % (min.-max.) | 1–3 | 1–3 | 3–5 |
| K$_2$O % (min.-max.) | 0–1 | 1–2 | 1–2 |
| CaO % (min.-max.) | 3–5 | 1–2 | 2–4 |
| Ignition Loss (max.) | 12% | 8% | 8% |

What is claimed is:

1. A process for preparing an injectable vegetable oil selected from the group consisting of soybean oil and sunflower oil and mixtures thereof which comprise:
   (a) first treating the vegetable oil at a temperature of 80° C. to about 130° C. with an acid clay;
   (b) deodorizing the vegetable oil with steam at a temperature of 220° C. to about 280° C. and applying a vacuum to remove volatilized components;
   (c) treating the deodorized vegetable oil, at a temperature of from about 10° C. to about 60° C., with an acid clay to reduce the content of a member selected from the group consisting of diglycerides, tocopherol components, and trilinolenin and mixtures thereof, wherein said acid clay is added in a weight ratio to said deodorized vegetable oil of from about 1:99 to about 1:1; and
   (d) thereafter conducting a particulate filtration to remove a substantial portion of the acid clay from the vegetable oil, wherein said filtration is accomplished with filters having a pore size of from about 0.1 to 0.45 microns,
thereby obtaining the injectable oil.

2. The process of claim 1 wherein the acid clay is a montmorillonite clay.

3. The process of claim 1 wherein the free fatty acid content of the injectable vegetable oil is increased after step (c).

4. The process of claim 1 wherein the injectable oil is soy oil.

5. The process of claim 1 wherein the deodorizing step is conducted utilizing steam at a temperature from about 240° C. to about 260° C.

6. The process of claim 1 wherein the filtration is conducted at from about 20° C. to about 40° C.

7. The process of claim 1 wherein the acid clay treatment (c) is conducted by passing the oil through a packed column.

* * * * *